United States Patent [19]
Yoshida et al.

[11] Patent Number: 5,931,802
[45] Date of Patent: Aug. 3, 1999

[54] EXTRACORPOREAL BLOOD CIRCULATOR

[75] Inventors: Eiichi Yoshida, Hyogo; Hiroshi Tachibana, Shiga; Takehisa Nakayama; Yasufumi Hamanishi, both of Hyogo; Yoshizumi Takao; Masataka Narisada, both of Tokyo, all of Japan

[73] Assignee: Kaneka Corporation, Osaka, Japan

[21] Appl. No.: 08/899,568

[22] Filed: Jul. 24, 1997

[30] Foreign Application Priority Data

Jul. 25, 1996 [JP] Japan ..................................... 8-195131

[51] Int. Cl.⁶ .................................................. A61M 37/00
[52] U.S. Cl. ................................................................ 604/4
[58] Field of Search ........................ 604/4–6; 422/44–48

[56] References Cited

U.S. PATENT DOCUMENTS

| | | | |
|---|---|---|---|
| 3,910,256 | 10/1975 | Clark et al. .................................. | 128/2 |
| 3,993,945 | 11/1976 | Warmoth et al. . | |
| 4,123,353 | 10/1978 | Hakansson et al. ....................... | 210/22 |
| 4,266,021 | 5/1981 | Nylen et al. ............................... | 435/14 |
| 4,322,275 | 3/1982 | Jain ......................................... | 204/180 |
| 4,353,368 | 10/1982 | Slovak et al. ............................ | 128/214 |
| 4,362,994 | 12/1982 | Goldsmith et al. . | |
| 4,791,932 | 12/1988 | Margules . | |
| 5,139,684 | 8/1992 | Kaali et al. ............................... | 210/748 |
| 5,165,406 | 11/1992 | Wong ....................................... | 128/635 |
| 5,215,519 | 6/1993 | Shettigar .................................... | 604/4 |
| 5,487,827 | 1/1996 | Peterson et al. .......................... | 210/87 |

FOREIGN PATENT DOCUMENTS 0 542 140 A2  11/1992  European Pat. Off. .
0 542 140 A3  11/1992  European Pat. Off. .

OTHER PUBLICATIONS

Communication from the European Patent Office, Sep. 1, 1998.

*Primary Examiner*—John G. Weiss
*Assistant Examiner*—Ki Yong O
*Attorney, Agent, or Firm*—Armstrong, Westerman, Hattori, McLeland & Naughton

[57] ABSTRACT

An extracorporeal blood circulator introducing blood collected from a body using a blood pump, subjecting a harmful substance contained in the collected blood to a predetermined treatment, and returning the thus-treated blood to the body, wherein electrodes of a conductivity meter used for monitoring the treatment are arranged on an outer surface of the extracorporeal blood circulator so as to be replaceable. The electrodes can be attached and detached with ease and disinfecting time and the number of process steps can be curtailed by arranging the electrode portion of the conductivity meter on an outer surface of the circulator.

4 Claims, 4 Drawing Sheets

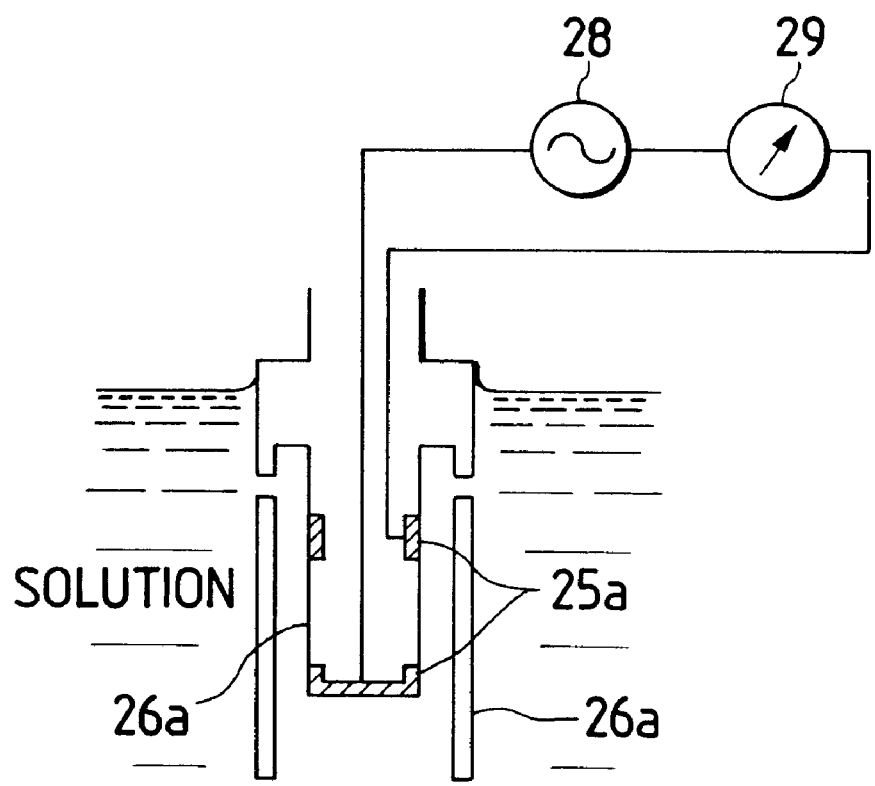

EXTRACORPOREAL BLOOD CIRCULATOR

BACKGROUND OF THE INVENTION

1. Field of the Invention

The present invention relates to an extracorporeal blood circulator that is easy to maintain. More particularly, the present invention is directed to an extracorporeal blood circulator having an improved structure for mounting the electrodes of a conductivity meter that monitors the conductivity of a cleaning solution flowing through an adsorbing unit.

2. Description of the Related Art

An extracorporeal blood circulator that provides the basis for the improvement of the present invention, particularly an apparatus of plasma pheresis (a blood plasma cleaner) will be described briefly with reference to FIGS. 2 and 3. In FIG. 2, reference character 1a denotes a blood collecting section for collecting blood from a brachium or the like (not shown) of a patient; and 1b, a blood returning section that returns the blood to the brachium or the like of the patient. The blood collected from the patient is mixed with an anticoagulant supplied from an anticoagulant injecting pump 2, and then conveyed to a blood plasma separator 4 by a blood pump 3. The blood plasma separator 4 separates the conveyed blood into blood plasma and blood cell component, with the blood plasma being conveyed to one of adsorbing units 6a, 6b (here, to the adsorbing unit 6a indicated by the solid line first) and with the blood cell component being conveyed to a mixing section 7.

The adsorbing unit 6a or 6b adsorbs only cholesterol in the blood plasma with a charged adsorbent. The thus treated blood plasma joins with the blood cell component at the mixing section 7, and is returned to the patient from the blood returning section 1b.

Since the adsorption of cholesterol is saturated after the adsorbing unit 6a or 6b has treated some hundreds of milliliters of blood plasma, the adsorbing units must be regenerated before saturation.

In order to regenerate the adsorbing unit 6a, not only the operation of adsorbing cholesterol is continued by the adsorbing unit 6b with the passage switched at a valve 8a to a dotted line A, the adsorbing unit 6b, a valve 8e, and a valve 8f in this sequence, but also a replacement solution within the adsorbing unit 6b is disposed of.

On the other hand, the replacement solution introduced from a replacement solution bag 12 flows to the adsorbing unit 6a via a passage followed by a valve 8c, an activation solution pump 11, a valve 8d, a dotted line C, the adsorbing unit 6a, a valve 8b, and the mixing section 7 in this sequence, so that the treated blood plasma within the adsorbing unit 6a is returned to the body of the patient.

Upon having returned the majority of the treated blood plasma within the adsorbing unit 6a to the body, not only the passage is switched so that an activation solution from an activation solution bag 10 flows via the valve 8c, the activation solution pump 11, the valve 8d, the dotted line C, the adsorbing unit 6a, the valve 8b, a dotted line D, the valve 8f in this sequence to be finally disposed of, but also regeneration of the adsorbing unit 6a is started.

Simultaneously therewith, the valve 8e is switched to a dotted line B on the adsorbing unit 6b side, so that the passage of the adsorbing unit 6b is switched to the mixing section 7 and the treated blood plasma is returned to the body. Further, when the adsorbing unit 6a has been regenerated with a predetermined quantity of activation solution introduced, the valve 8c is switched to the replacement solution bag side, not only causing the replacement solution to drive the activation solution away from the adsorbing unit 6a, but also causing the replacement solution to clean the adsorbing unit 6a and supply the adsorbing unit 6a with the replacement solution until the adsorbing unit 6b performs the treatment up to 600 ml.

On the other hand, the adsorbing unit 6b continuously performs the adsorbing operation under the same condition until the adsorbing unit 6b performs the operation up to 600 ml. Here, only for a period during which some tens of milliliters immediately before the amount of treatment reaches 600 ml, the passage is switched by the valve 8f, so that the replacement solution to be disposed of is caused to flow to the conductivity meter 20a to thereby measure the conductivity of the replacement solution.

The adsorbing units 6b, 6a thereafter repeat the same regenerating operation alternately, switching the passages correspondingly. Conductivity measurements are made to check that the activation solution having high salt concentration is replaced with the replacement solution (0.9% physiological saline). This check is made every time the adsorbing units 6a, 6b are regenerated. Once a medical treatment has been finished, a disinfecting solution is charged into the conductivity meter 20a, so that the electrodes of the conductivity meter 20a which are likely to be contaminated with blood plasma are disinfected.

FIG. 3 is a diagram showing the construction of the front side of a panel of the apparatus of plasma pheresis. The same parts and components as those of FIG. 2 are denoted by the same reference numerals. As shown in FIG. 3, the anticoagulant pump 2, the pumps for blood, blood plasma, activation solution (3, 5, 11), the blood plasma separator 4, the adsorbing units 6a, 6b, a humidifier 14, the respective valves 8, and the tubes for connecting these valves are attached to the front side of the panel, whereas parts contaminated with blood and harmful substance (materies morbi) and the like contained in blood (exemplary parts being the blood plasma separator 4, the adsorbing units 6a, 6b, the tubes through which blood flows, and the like) are disposable. Thus, the disposable parts are designed to be easily attached and detached.

The conductivity meter 20a used for such extracorporeal blood circulator is arranged inside the circulator. FIG. 4 shows the concept of an ordinary conductivity meter. That is, FIG. 4 is a sectional view showing a main portion of an electrode portion of the conductivity meter. Conductivity is measured by dipping the electrodes into a solution to be measured, energizing a dc current of an ac current from a power supply 28 between a pair of electrodes 25a disposed in an insulated sleeve 26a, and measuring the quantity of electricity between the electrodes with an electric meter 29. If ion concentration is low, salt concentration in the cleaning solution flowing through the adsorbing units 6 can be measured since conductivity is proportional to ion concentration.

The conductivity meter is disinfected during every medical treatment. Such disinfecting operation is performed by injecting a disinfecting solution to the electrode portion from the front side of the panel, then leaving the electrode portion as it is for about an hour, and thereafter cleaning the electrode portion with the replacement solution. Therefore, there exists the problem that the disinfecting operation involves a number of steps and is time-consuming.

SUMMARY OF THE INVENTION

The present invention has been made to overcome the aforementioned problem. The object of the present invention is, therefore, to provide an extracorporeal blood circulator in which electrodes can be attached and detached with ease and disinfecting time and the number of disinfecting process steps can be curtailed by arranging the electrode portion of the conductivity meter on an outer surface of the circulator.

To achieve the above object, the present invention is applied to an extracorporeal blood circulator that introduces blood collected from a body using a blood pump, subjects a harmful substance contained in the collected blood to a predetermined treatment, and returns the thus treated blood to the body. In such an extracorporeal blood circulator, electrodes of a conductivity meter used for monitoring the treatment are arranged on an outer surface of the extracorporeal blood circulator so as to be replaceable.

BRIEF DESCRIPTION OF THE DRAWINGS

FIG. 4 is a diagram illustrative of the concept of a conductivity meter.

DETAILED DESCRIPTION OF THE PREFERRED EMBODIMENT

Figure 1A:
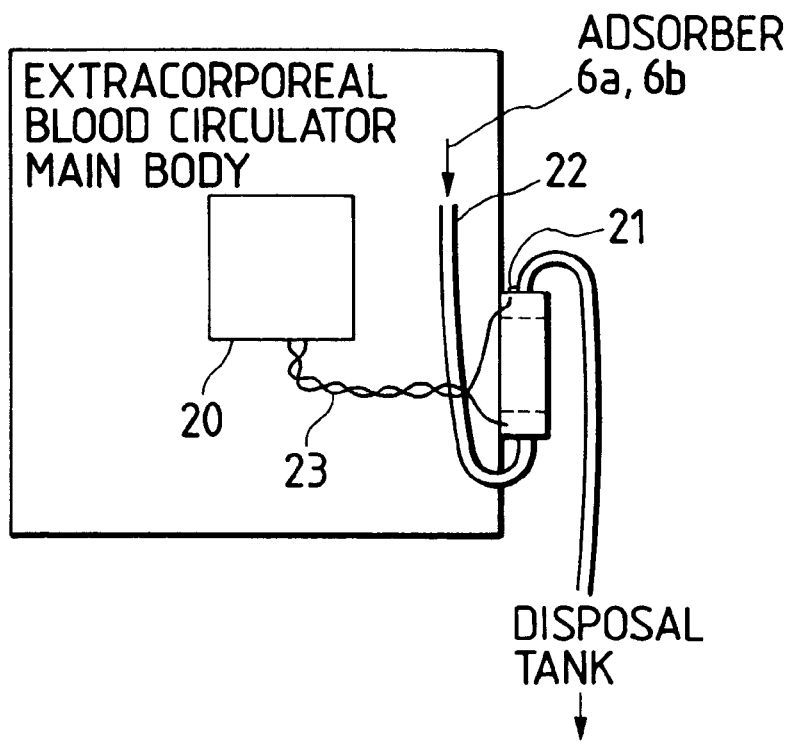
FIGS. 1A and 1B are diagrams showing the construction of a main portion of an extracorporeal blood circulator, which is an embodiment of the present invention.
Figure 1B:
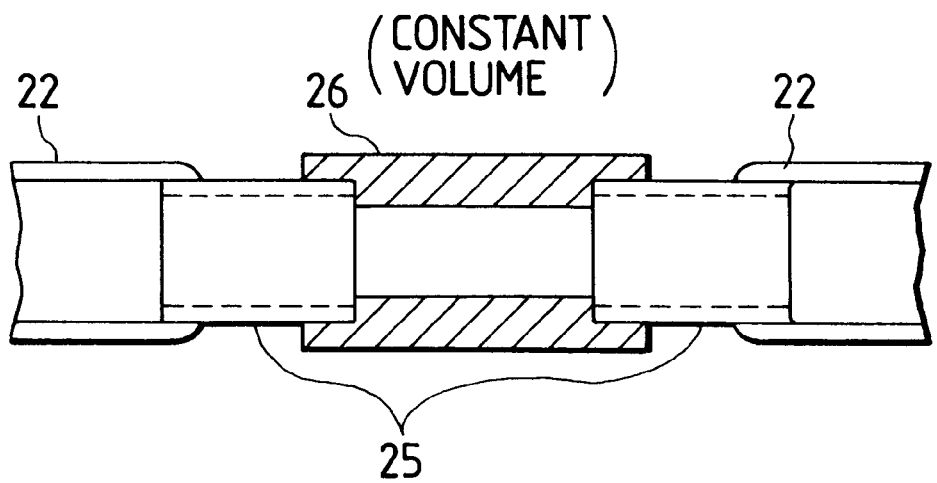
Figure 2:
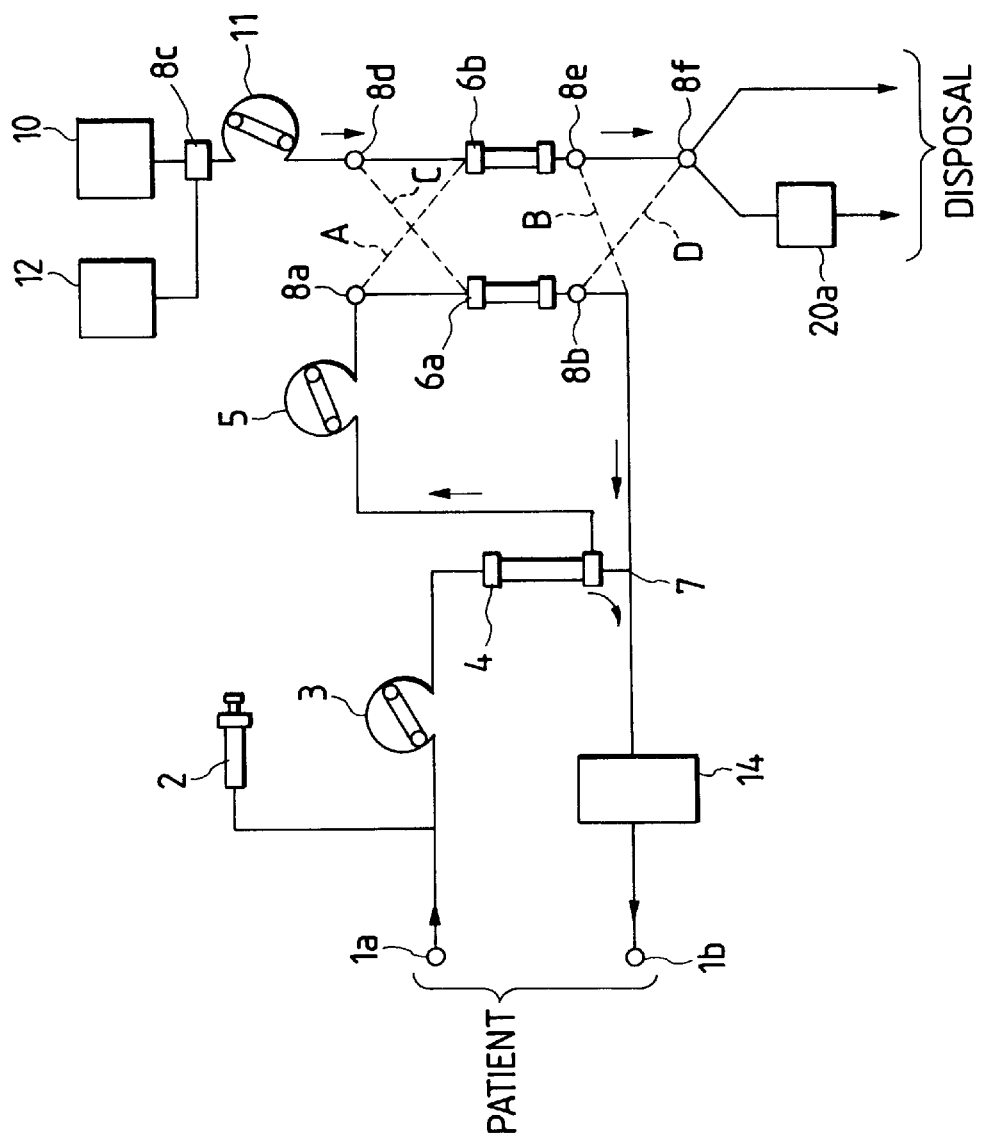
FIG. 2 is a diagram illustrative of the construction of an exemplary extracorporeal blood circulator.
Figure 3:
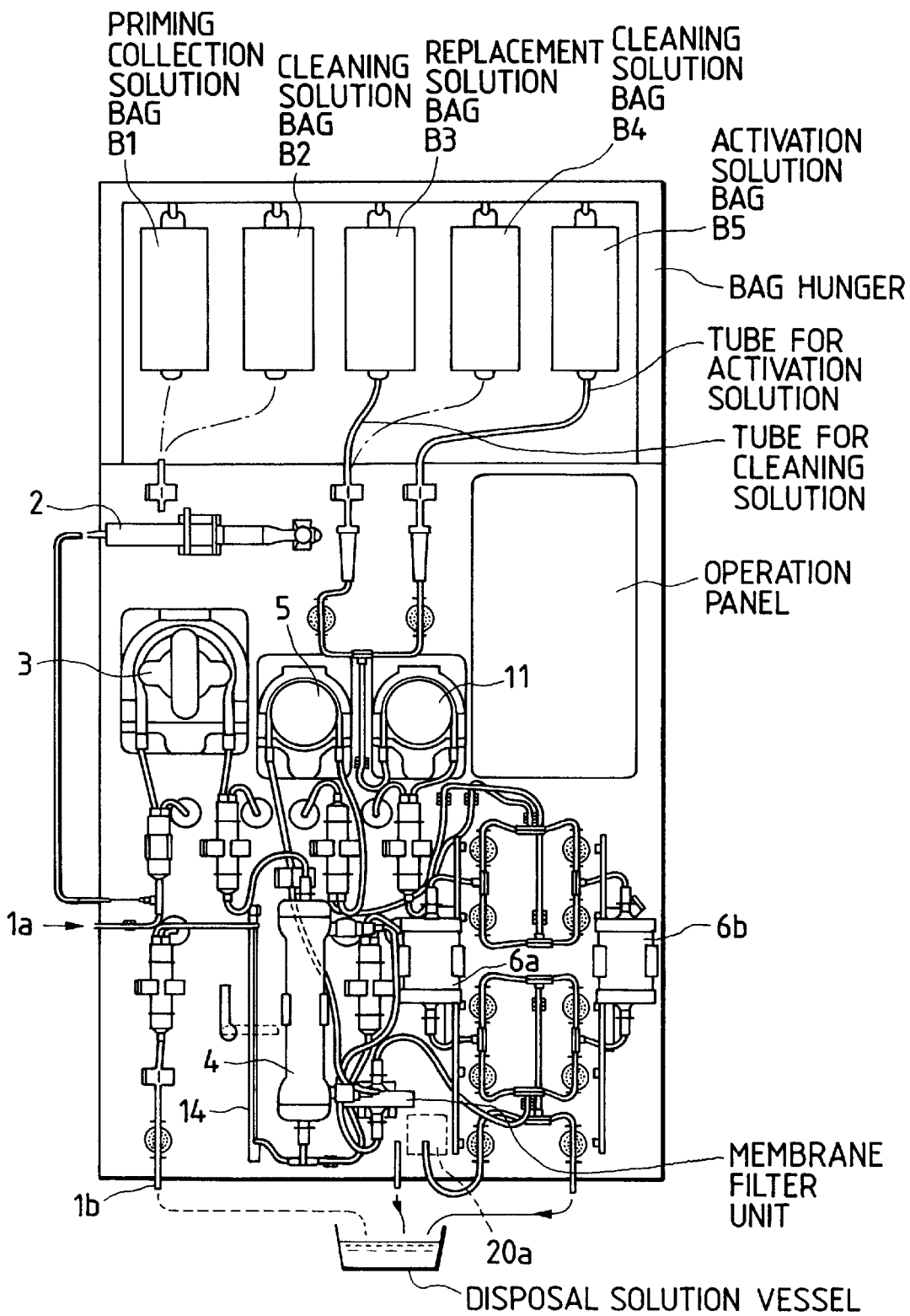
FIG. 3 is a diagram illustrative of the arrangement of parts of the exemplary extracorporeal circulator.

FIGS. 1A and 1B and diagrams showing the construction of a main portion of an embodiment of the present invention. Since the construction of parts and components other than a conductivity meter is similar to that of the example, the descriptions thereof will be omitted. FIG. 1A shows an electrode portion of a conductivity meter 20 disposed within a circulator arranged on an outer side surface of the circulator. The electrode portion is fixed to an electrode holder 21. Reference numeral 22 denotes a tube through which an activation solution or a replacement solution flows; 23, electric wires, one end of each wire being connected to the electrode holder 21 and the other end of each wire being connected to an electric meter (e.g., an ammeter) of the conductivity meter 20.

FIG. 1B is a diagram showing the construction of a main portion of an electrode of the conductivity meter to be used in the present invention. In FIG. 1B, reference numeral 22 denotes the tube that is made of, e.g., vinyl chloride; 25, cylindrical electrodes; and 26, a cylindrical insulating plastic member, both ends of which allow the electrodes 25 to be hermetically inserted thereinto. The insulating plastic member 26 is formed so that the internal capacity is fixed.

As shown in FIG. 1A, the tube on both ends is such that one end thereof is connected to adsorbing units 6 and the other end thereof is connected to a waste tank. These electrodes 25 are held in the electrode holder 21 shown in FIG. 1A. Therefore, by removing the electrodes 25 and the tube 22 from the electrode holder 21 together with the adsorbing unit 6 that is replaced during every medical treatment, only the electrodes can be replaced easily.

In the aforementioned construction, ion concentration can be detected by a replacement solution (cleaning solution) passing through the electrodes 25, the replacement solution having already passed through the adsorbing units 6a, 6b, and thus, the fact that the activation solution has been replaced with the replacement solution can be confirmed. It may be noted that the electrode holder 21 may be arranged on the front panel or at any arbitrarily selected place.

As described in the foregoing in detail, the present invention is characterized in that the electrodes of a conductivity meter that is used for monitoring a replacement solution (cleaning solution) of adsorbing units are replaceably arranged on an outer surface of the circulator. As a result of this construction, the following advantages can be obtained:

(1) Disinfection of the electrode portion can be omitted.

(2) Risks of infection in the case of failure to disinfect can be avoided.

(3) Since the disinfecting operation is omitted, maintenance of the circulator becomes simple.

(4) In contrast to the example in which, having to go through the disinfection process, conductivity of a solution in the final stage had to be measured, the present invention can implement an extracorporeal blood circulator that can continuously monitor the waste solution from start to end because the electrode portion is disposable.

What is claimed is:

1. An extracorporeal blood circulator introducing blood collected from a body using a blood pump, subjecting a harmful substance contained in the blood to a predetermined treatment, and returning the thus treated blood to the body, comprising:

a conductivity meter used for monitoring the treatment comprising electrodes, an electrodes holder holding said electrodes, and an extracorporeal circuit comprising tubing, the tubing having an inside surface and an outside surface, wherein said electrodes are attached directly to an inside surface of the tubing so as to be replaceable from said electrodes holder.

2. The circulator according to claim 1, wherein each of said electrodes has a cylindrical configuration inside of which solution to be checked can flow.

3. The circulator according to claim 2, wherein a cylindrical insulative member is interposed between said electrodes.

4. The circulator according to claim 1, wherein said electrodes are removably mounted between two tubes so that a solution to be checked flows from one of said two tubes through said electrodes to the other of said two tubes.

* * * * *